(12) United States Patent
Chen et al.

(10) Patent No.: US 8,313,534 B1
(45) Date of Patent: Nov. 20, 2012

(54) ARTIFICIAL KNEE JOINT

(75) Inventors: Shen-Yi Chen, New Taipei (TW);
Chun-Sen Han, New Taipei (TW)

(73) Assignee: Chang-Yu Mechanical System Ltd., New Taipei (TW)

( * ) Notice: Subject to any disclaimer, the term of this patent is extended or adjusted under 35 U.S.C. 154(b) by 12 days.

(21) Appl. No.: 13/176,399

(22) Filed: Jul. 5, 2011

(51) Int. Cl.
*A61F 2/64* (2006.01)
(52) U.S. Cl. .......................................... 623/43
(58) Field of Classification Search ............... 623/39–46; 602/27
See application file for complete search history.

(56) References Cited

U.S. PATENT DOCUMENTS

| | | | |
|---|---|---|---|
| 4,178,642 A * | 12/1979 | May | ................................ 623/45 |
| 5,314,498 A | 5/1994 | Gramnas | |
| 5,728,173 A | 3/1998 | Chen | |
| 7,066,964 B2 | 6/2006 | Wild | |
| 7,833,285 B2 * | 11/2010 | Reinhardt | ........................ 623/39 |
| 2003/0195637 A1 * | 10/2003 | Shen | ............................... 623/44 |
| 2008/0071388 A1 * | 3/2008 | Chen | ............................... 623/44 |

* cited by examiner

*Primary Examiner* — Bruce E Snow
(74) *Attorney, Agent, or Firm* — Wang Law Firm, Inc.; Li K. Wang; Stephen Hsu

(57) ABSTRACT

An artificial knee joint includes a four-bar linkage, an extension bar having a first end pivotally connected to the four-bar linkage, and a restoring device connected to a bottom of the four-bar linkage and comprising a transmission rod having a first end pivotally connected to and retractably moving a second end of the extension bar. The four-bar linkage includes a first, second, third, and fourth connecting bar, any two adjacent connecting bars of which are connected together by their respective pivot axles. When the four-bar linkage is moved to a locked state, a specific included angle is defined between any two adjacent straight lines joining adjacent pivot axles of the four-bar linkage. While walking, an artificial leg of an artificial limb using the artificial knee joint does not produce unexpected wobbles in the swing phase, and the artificial limb can provide enough support in the stance phase.

4 Claims, 10 Drawing Sheets

A    B    C    D    E    F    G    H

ARTIFICIAL KNEE JOINT

BACKGROUND OF THE INVENTION

1. Field of the Invention

The present invention relates to an artificial knee joint, and more particularly to an artificial knee joint that can be operated or controlled by a user's residual limb in an agile and stable manner.

2. The Prior Arts

Prostheses usually are used to replace a missing body part, such as a limb, a tooth, an eye, or a heart valve, for compensating lost functions thereof. The artificial limbs are usually made of aluminum, wooden materials, leather, plastics, or the like materials, and have joints comprised of metallic parts. Recently, the dominated materials used to manufacture the artificial limbs include titanium alloys and carbon fiber materials.

Most of conventional artificial knee joints used in the artificial limbs include a single-axle structure. In case the artificial knee joint is assembled too loose, the artificial limb may produce unexpected wobbles when it is raised during walking, or provide not enough support when it is in contact with the ground. In contrast, if the artificial knee joint is assembled too tight, the artificial limb may not take steps forward in agile manner during walking. As a result, the users wearing the conventional artificial limbs will require additional energy, and may incur risk of accidental falls.

Therefore, it is desired to provide an improved artificial knee joint that can solve the aforementioned disadvantages.

SUMMARY OF THE INVENTION

A primary objective of the present invention is to provide an artificial knee joint that can be operated or controlled by a user's residual limb in an agile and stable manner, so as to solve the aforementioned disadvantages.

In order to achieve the aforementioned objective, an artificial knee joint according to the present invention comprises a four-bar linkage, an extension bar having a first end pivotally connected to the four-bar linkage, and a restoring device connected to a bottom of the four-bar linkage and comprising a transmission rod having a first end pivotally connected to and retractably moving a second end of the extension bar. The four-bar linkage comprises a first connecting bar, a second connecting bar, a third connecting bar, and a fourth connecting bar, wherein a first end of a first connecting bar and a second end of a second connecting bar are pivotally connected together by a first pivot axle, a first end of a second connecting bar and a second end of a third connecting bar are pivotally connected together by a second pivot axle, a first end of a third connecting bar and a second end of a fourth connecting bar are pivotally connected together by a third pivot axle, and a first end of a fourth connecting bar and a second end of a first connecting bar are pivotally connected together by a fourth pivot axle. A first straight line joins the first pivot axle and the second pivot axle, a second straight line joins the second pivot axle and the third pivot axle, a third straight line joins the third pivot axle and the fourth pivot axle, and a fourth straight line joins the fourth pivot axle and the first pivot axle. The first end of the extension bar is pivotally connected to the fourth pivot axle. By means of the actions of gravity and the restoring device on the extension bar and further on the fourth pivot axle, the four-bar linkage is expanded to a limited state or a locked state. At this moment, an included angle $\theta_1$ defined between the first straight line and the second straight line is between 21°-23°, an included angle $\theta_2$ defined between the second straight line and the third straight line is between 159°-161°, an included angle $\theta_3$ defined between the third straight line and the fourth straight line is between 97°-99°, and an included angle $\theta_4$ defined between the fourth straight line and the first straight line is between 78°-80°.

According to an embodiment of the present invention, the restoring device further comprises a body and an extension-biasing spring. The extension-biasing spring and the transmission rod are assembled in the body, a first end of extension-biasing spring is biased against a second end of the transmission rod and a second end of the extension-biasing spring is biased against a bottom of the body.

According to another embodiment of the present invention, the restoring device can be a pneumatic cylinder or a hydraulic cylinder having a transmission rod, which can be retractably moved. One end of the transmission rod is pivotally connected to and retractably moves a second end of the extension bar.

For an artificial limb using the artificial knee joint according to the above included angle design of the present invention, while walking, the artificial leg of the artificial limb does not produce unexpected wobbles in the swing phase, and the artificial limb can provide enough support in the stance phase. In addition, the artificial limb can be operated or moved in agility, thereby saving the user's energy and reducing occurrence of accidental falls.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENTS

Figure 1:
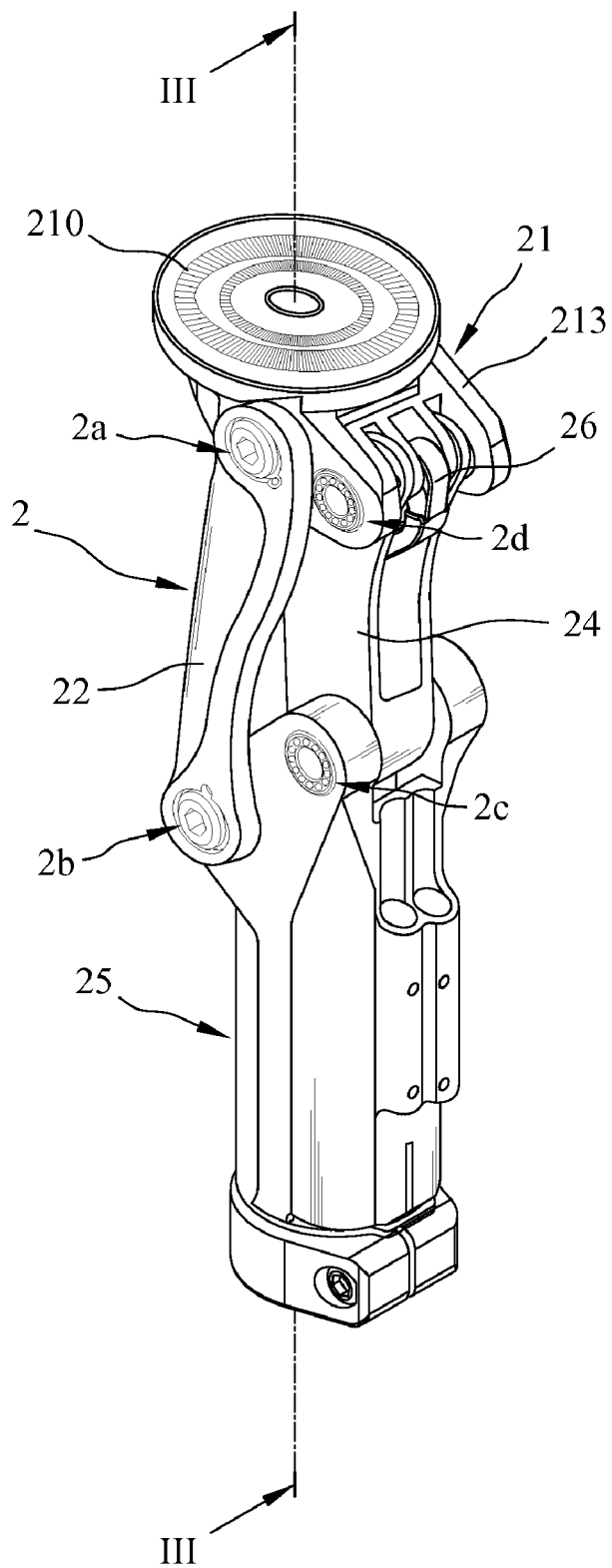
FIG. 1 is a perspective view of an artificial knee joint according to an embodiment of the present invention.
Figure 2:
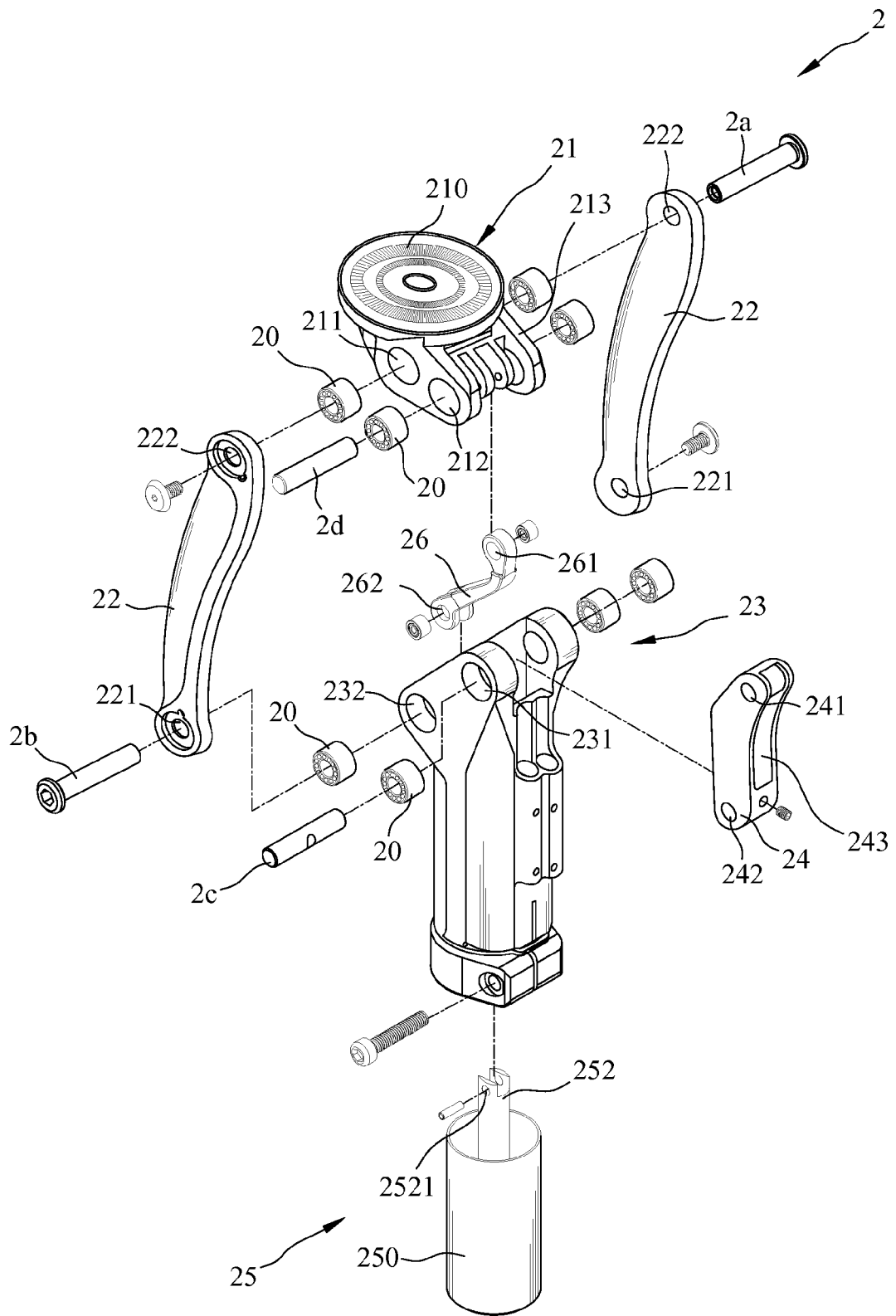
FIG. 2 is an exploded perspective view of the artificial knee joint according to the present invention.

FIG. 1 is a perspective view of an artificial knee joint according to an embodiment of the present invention. FIG. 2 is an exploded perspective view of the artificial knee joint according to the present invention. The artificial knee joint according to the present invention comprises a four-bar linkage 2, an extension bar 26 having a first end pivotally connected to the four-bar linkage 2, and a restoring device 25 assembled to a bottom of the four-bar linkage 2. The restoring device 25 comprises a transmission rod 252 having a first end pivotally connected to and retractably moving a second end of the extension bar 26. The four-bar linkage 2 comprises a first connecting bar 21, a second connecting bar 22, a third connecting bar 23, and a fourth connecting bar 24. The first connecting bar 21 has two symmetrical sidewalls 213 spaced apart from each other. The two sidewalls 213 each have an opposite first pivot A-hole 211 and an opposite pivot B-hole 212. The first connecting bar 21 further includes a load portion 210 on a top thereof, to which a socket 1 can be assembled. The socket 1 can be adapted to receive a residual limb.

The second connecting bar 22 includes two sets of bars. The second connecting bar 22 has a second pivot A-hole 221 and a second pivot B-hole 222 respectively located on two opposite ends thereof. An inner side of the first pivot A-hole 211 of the first connecting bar 21 is assembled with a bearing 20. A first pivot axle 2a is passed through the second pivot B-hole 222 of the second connecting bar 22 and the bearing 20 in the first pivot A-hole 211 of the first connecting bar 21 to pivotally connect the first connecting bar 21 and the second connecting bar 22.

The third connecting bar 23 has two symmetrical sidewalls spaced apart from each other. The two sidewalls each have an opposite third pivot A-hole 231 and an opposite third pivot B-hole 232. An inner side of the third pivot B-hole 232 of the third connecting bar 23 is assembled with a bearing 20. A second pivot axle 2b is passed through the second pivot A-hole 221 of the second connecting bar 22 and the bearing 20 in the third pivot B-hole 232 of the third connecting bar 23 to pivotally connect the second connecting bar 22 and the third connecting bar 23.

The fourth connecting bar 24 has a through slot 243 on a center thereof and a fourth pivot A-hole 241 and a fourth pivot B-hole 242 respectively located on two opposite ends thereof. An inner side of the third pivot A-hole 231 of the third connecting bar 23 is assembled with a bearing 20. A third pivot axle 2c is passed through the bearing 20 in the third pivot A-hole 231 of the third connecting bar 23 and the fourth pivot B-hole 242 of the fourth connecting bar 24 to pivotally connect the third connecting bar 23 and the fourth connecting bar 24.

An inner side of the first pivot B-hole 212 of the first connecting bar 21 is assembled with a bearing 20. A fourth pivot axle 2d is passed through the bearing 20 in the first pivot B-hole 212 of the first connecting bar 21 and the fourth pivot A-hole 241 of the fourth connecting bar 24 to pivotally connect the fourth connecting bar 24 and the first connecting bar 21.

Figure 3:
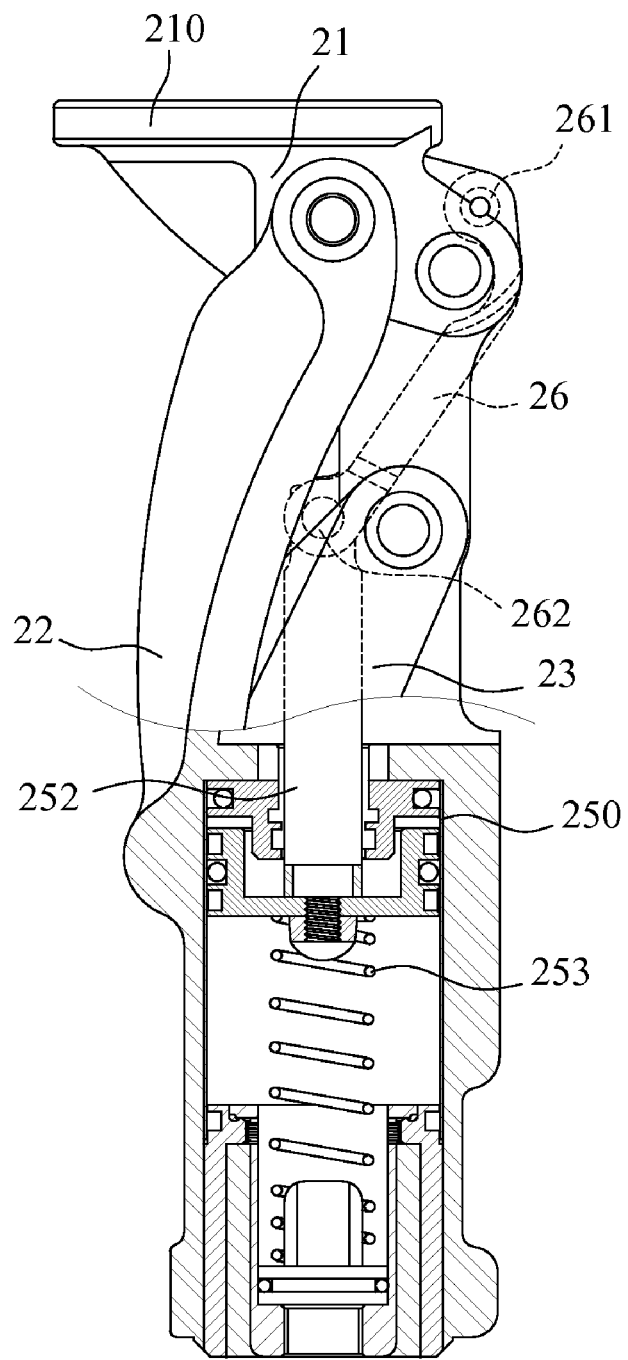
FIG. 3 is a partially cross sectional view showing a restoring device is received in the artificial knee joint according to the present invention.

As described in the above, the restoring device 25 is assembled to a bottom of the four-bar linkage 2. More specifically, the third connecting bar 23 has an inner space defined therethrough in the vertical direction for receiving the restoring device 25 (see FIG. 3). The restoring device 25 according to an embodiment of the present invention further comprises a body 250 and an extension-biasing spring 253. The extension-biasing spring 253 and the transmission rod 252 are assembled in the body 250. A first end of the extension-biasing spring 253 is biased against a second end of the transmission rod 252 and a second end of the extension-biasing spring 253 is biased against a bottom of the body 250. A lower end of the restoring device 25 can be assembled with an artificial leg 3, and a lower end of the artificial leg 3 can be assembled with an artificial foot 4 (see FIG. 6).

The extension bar 26 has a first through hole 261 and a second through hole 262 respectively located on two opposite ends thereof. The extension bar 26 is assembled through the through slot 243 of the fourth connecting bar 24, and the first through hole 261 of the extension bar 26 is pivotally connected with the fourth pivot axle 2d and the second through hole 262 of the extension bar 26 is pivotally connected to the first end of the transmission rod 252 by a pivot axle. When the artificial knee joint is kept unbent and no load is applied thereto, the four-bar linkage 2 is expanded to a limited state or a locked state under the actions of gravity and the biasing force applied by the extension-biasing spring 253 onto the transmission rod 252 and further onto the fourth pivot axle 2d.

According to another embodiment of the present invention, the restoring device 25 can be a pneumatic cylinder or a hydraulic cylinder having a transmission rod, which can be retractably moved. One end of the transmission rod is pivotally connected to and retractably moves a second end of the extension bar 26.

Figure 4:
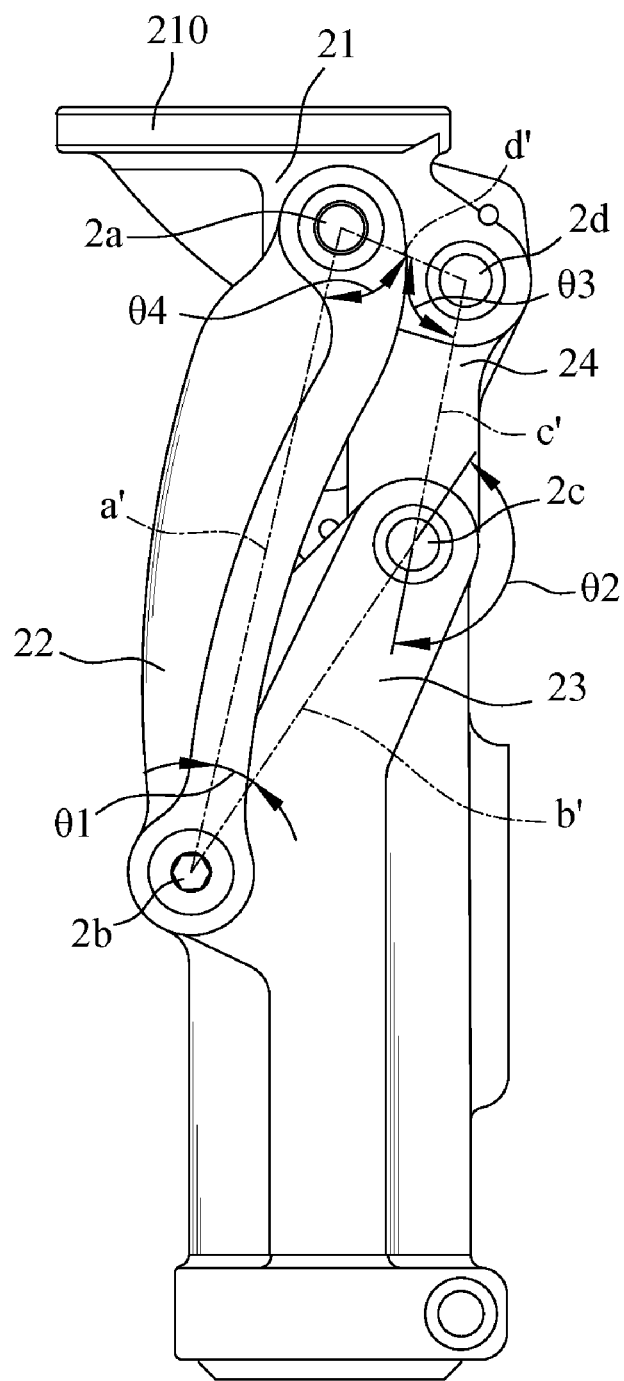
FIG. 4 is a schematic view showing included angles defined between two adjacent straight lines joining adjacent pivot axles of a four-bar linkage according to the present invention.

As shown in FIG. 4, a first straight line a' joins the first pivot axle 2a and the second pivot axle 2b, a second straight line b' joins the second pivot axle 2b and the third pivot axle 2c, a third straight line c' joins the third pivot axle 2c and the fourth pivot axle 2d, and a fourth straight line d' joins the fourth pivot axle 2d and the first pivot axle 2a. Under the action of gravity and the biasing force applied by the extension-biasing spring 253 on the fourth pivot axle 2d, the four-bar linkage 2 is expanded to a limited state or a locked state. At this moment, an included angle $\theta_1$ defined between the first straight line a' and the second straight line b' is between 21°-23°, an included angle $\theta_2$ defined between the second straight line b' and the third straight line c' is between 159°-161°, an included angle $\theta_3$ defined between the third straight line c' and the fourth straight line d' is between 97°-99°, and an included angle $\theta_4$ defined between the fourth straight line d' and the first straight line a' is between 78°-80°.

Figure 5:
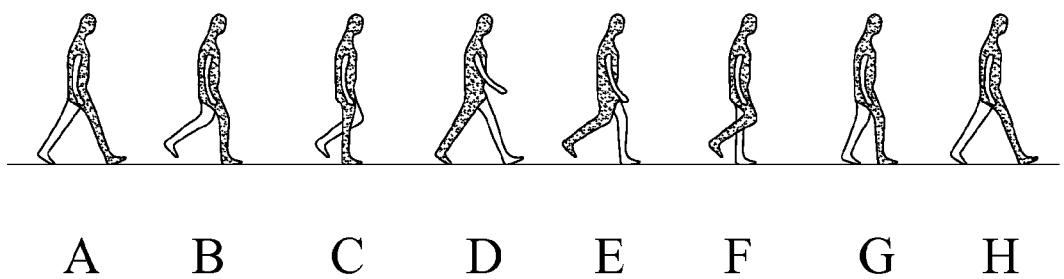
FIG. 5 is a schematic view showing intermediate stages in a typical gait cycle.

FIG. 5 is a schematic view showing intermediate stages in a typical gait cycle. Stages A through H illustrate a gait cycle performed by the right leg. Suppose that the right leg is the artificial leg, stages A through D define a stance phase, and stages E through H define a swing phase. In the stance phase, the four-bar linkage is in a locked state to provide support. As the artificial leg steps forward in stage D (which indicates entry into the swing phase), the forward step of the artificial leg causes the four-bar linkage to be self unlocked for allowing the artificial knee joint to be bent. As a result, the artificial leg can raise and then step forward.

Figure 6:
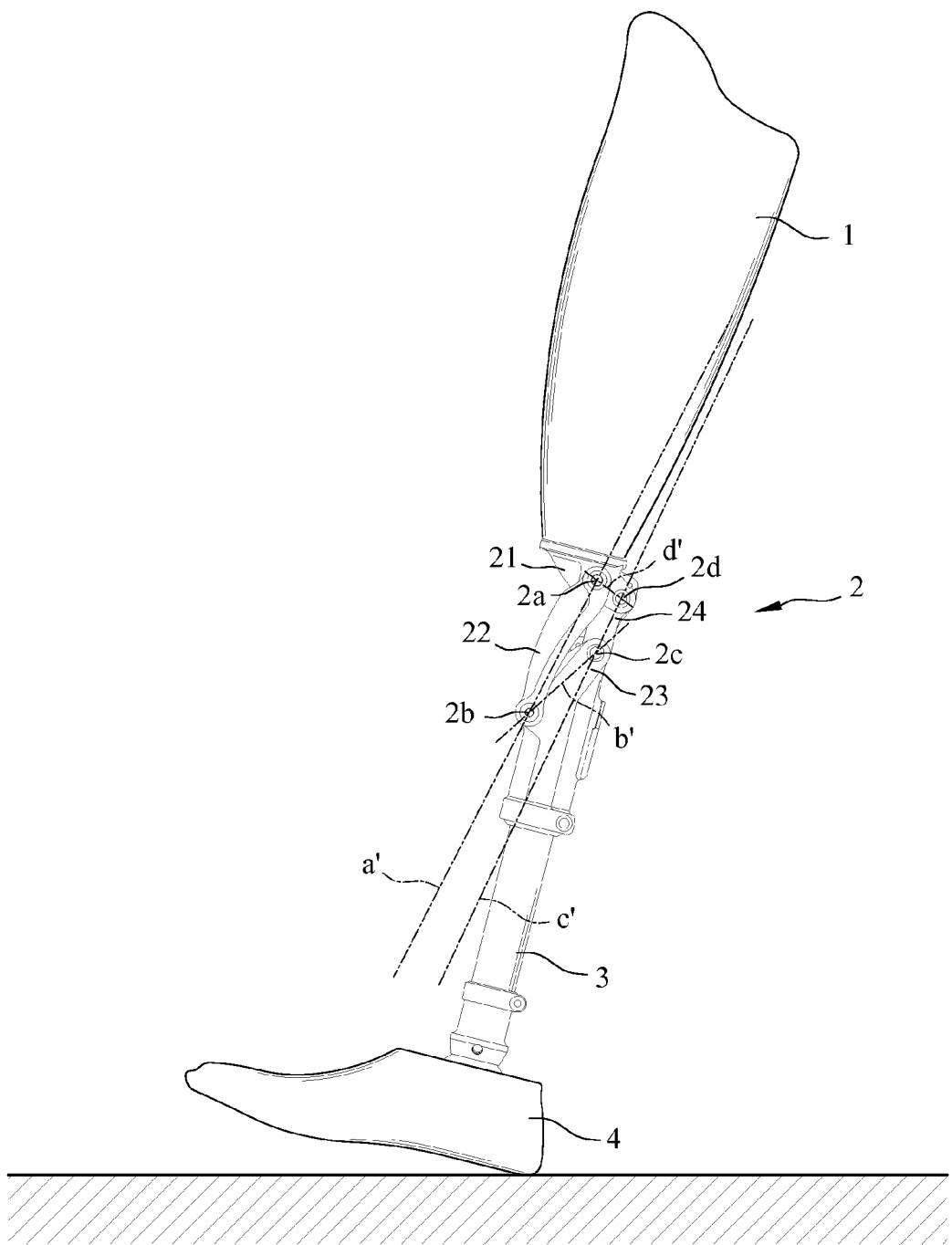
FIG. 6 is a schematic view showing when the socket is not raised, the artificial knee joint is in a locked state to provide support for the user's weight.
Figure 7:
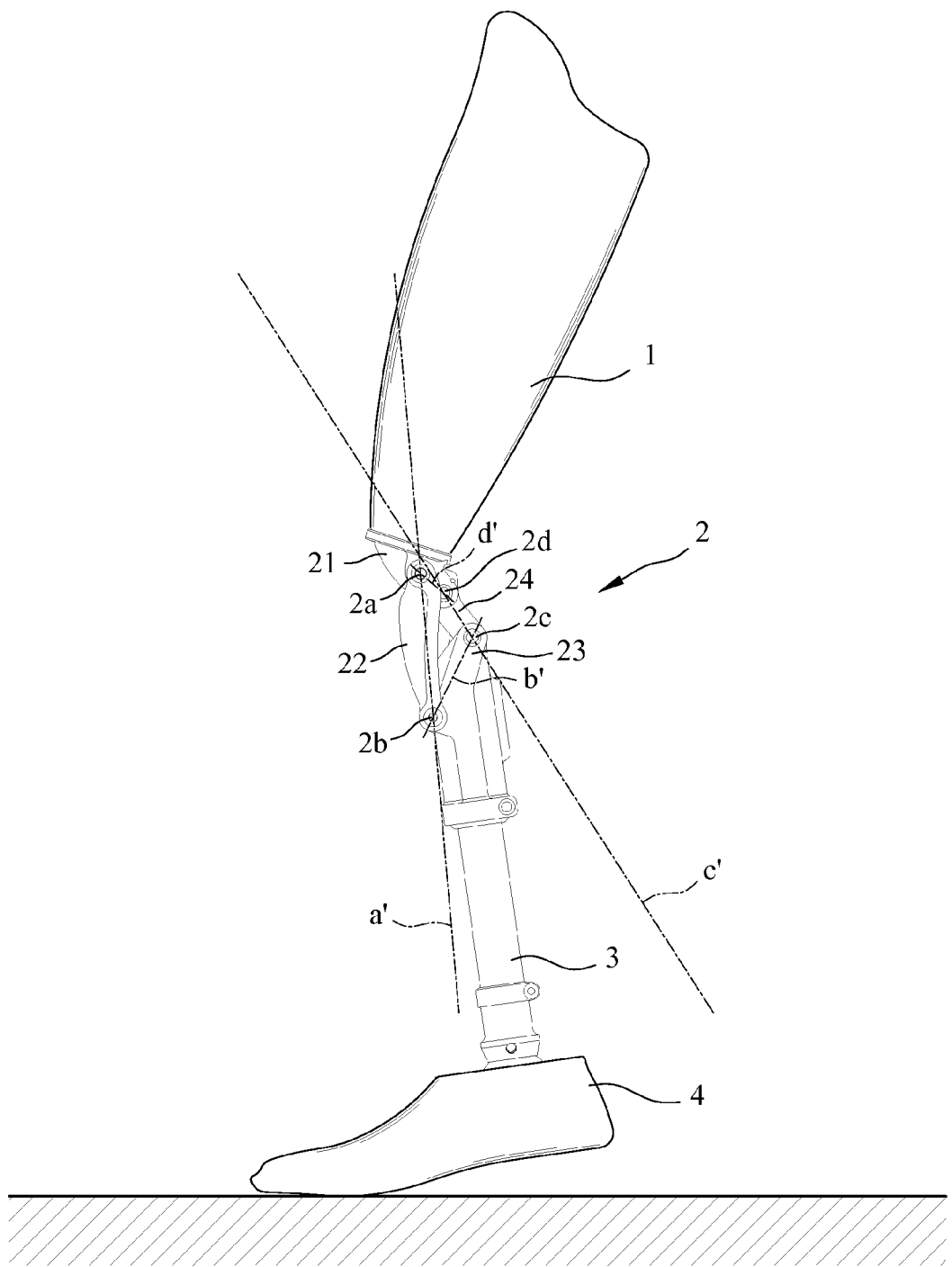
FIG. 7 is a schematic view showing when the socket is raised, the artificial knee joint is self unlocked to enable it to be bent.

Referring to FIG. 6, the residual limb can be fitted into the socket 1. When the user starts to step forward and a heel of the artificial foot 4 contacts with the ground, the third straight line c' of the four-bar linkage 2 is inclined rearward such that the center of gravity is shifted rearward, which causes the four-bar linkage 2 to be kept in a locked state. As such, a pivotal rotation around the first pivot axle 2a, the second pivot axle 2b, the third pivot axle 2c, and the fourth pivot axle 2d will not occur, so that the four-bar linkage 2 can provide stable support to sustain the user's weight. As the residual limb or the socket 1 swings forward, the forward swing of the socket 1 generates a torque about the first pivot axle 2a and the second pivot axle 2b to drive the four-bar linkage 2 to move and make the artificial knee joint bent (see FIG. 7). When the socket 1 stops swinging forward, the four-bar linkage recovers to the locked state (see FIG. 6) due to the action of gravity and the biasing force applied by the extension-biasing spring 253 on the fourth pivot axle 2d. As such, once a bottom of the artificial foot contacts with the ground, the artificial knee joint can provide an effective support to sustain the user's weight.

Figure 8:
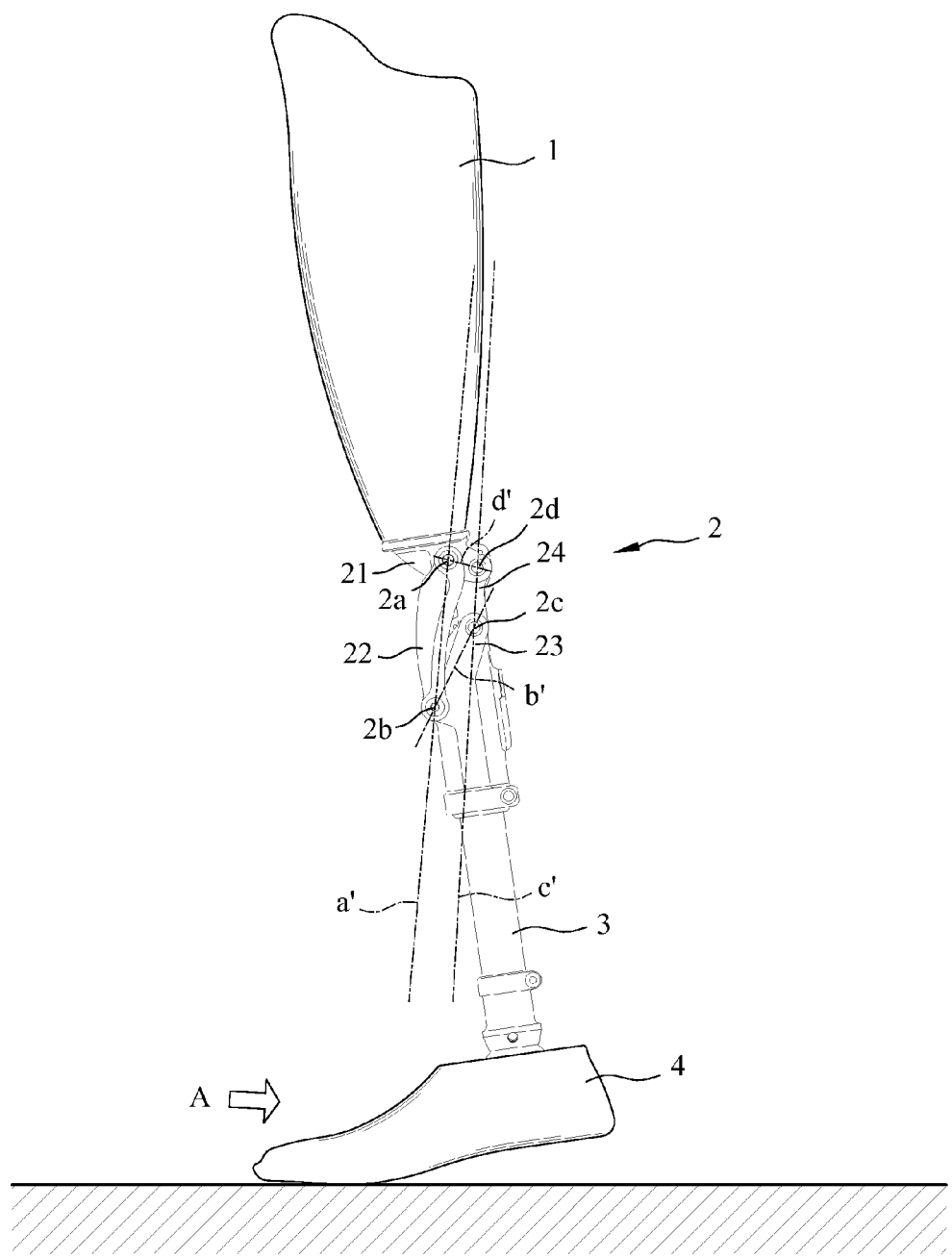
FIG. 8 is a schematic view showing when the third straight line c' gradually becomes perpendicular to the ground, how a reaction force A is applied to toes of the artificial foot by the ground.

As shown in FIG. 8, when the other leg of the user steps forward, the artificial leg supporting the user's weight is shifted to a position at a rear of the user, and the toes of the artificial foot 4 contact with the ground. At this moment, a reaction force A is applied to the toes of the artificial foot 4 by the ground and the third straight line c' gradually becomes perpendicular to the ground. When the reaction force A becomes to be perpendicular to the third straight line c', the reaction force A will release the lock of the third pivot axle 2c and the fourth pivot axle 2d, and due to the linkage mechanism, then release the lock of the first pivot axle 2a and the second pivot axle 2b, thereby the four connecting bars 21, 22, 23, and 24, and the extension bar 26 will be pivotally rotated about their respective pivot axles to allow the artificial knee joint to be bent. As a result, the artificial leg can raise and then start to step forward. When the artificial leg steps forward, all of the members of the artificial knee joint recover to the original positions or the locked state as shown in FIG. 6, so as to repeat the gait cycle.

For an artificial limb using the artificial knee joint according to the present invention, while walking, the artificial leg of the artificial limb does not produce unexpected wobbles in the swing phase, and the artificial limb can provide enough support in the stance phase. In addition, the artificial limb can be operated or moved in agility, thereby saving the user's energy and reducing occurrence of accidental falls.

Figure 9:
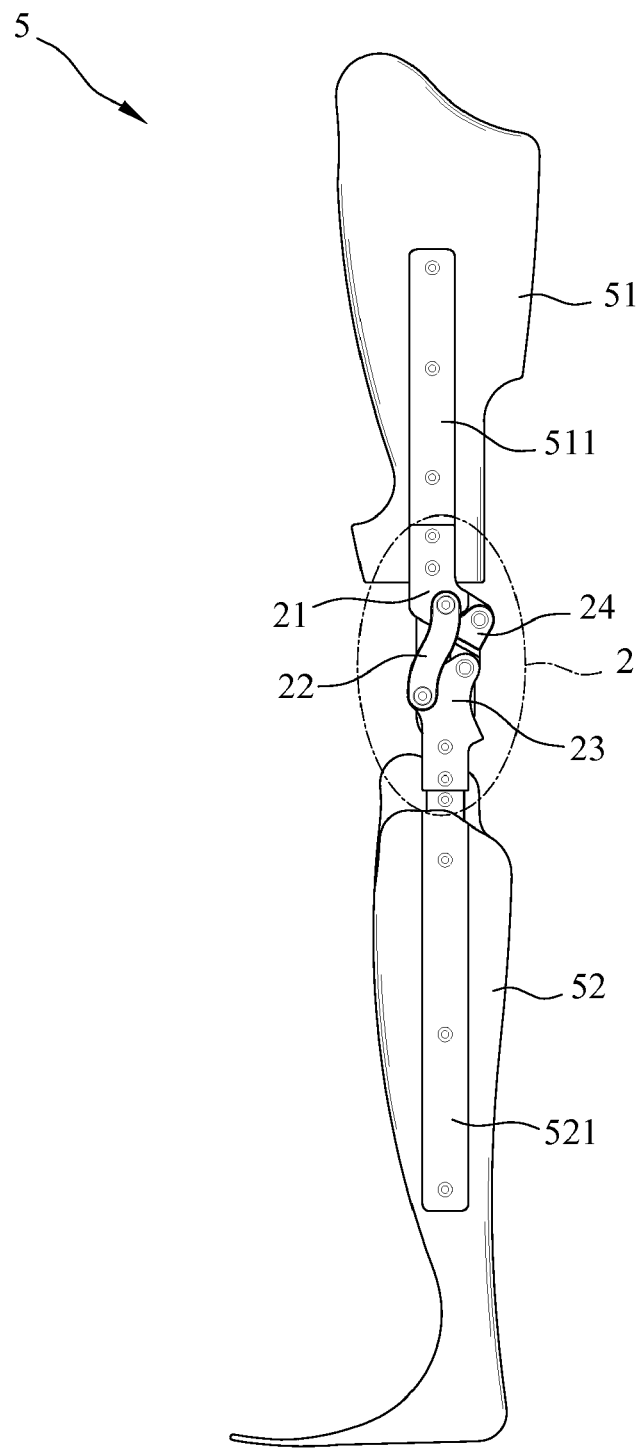
FIG. 9 is a schematic view showing the artificial knee joint according to the present invention is assembled in a leg brace.
Figure 10:
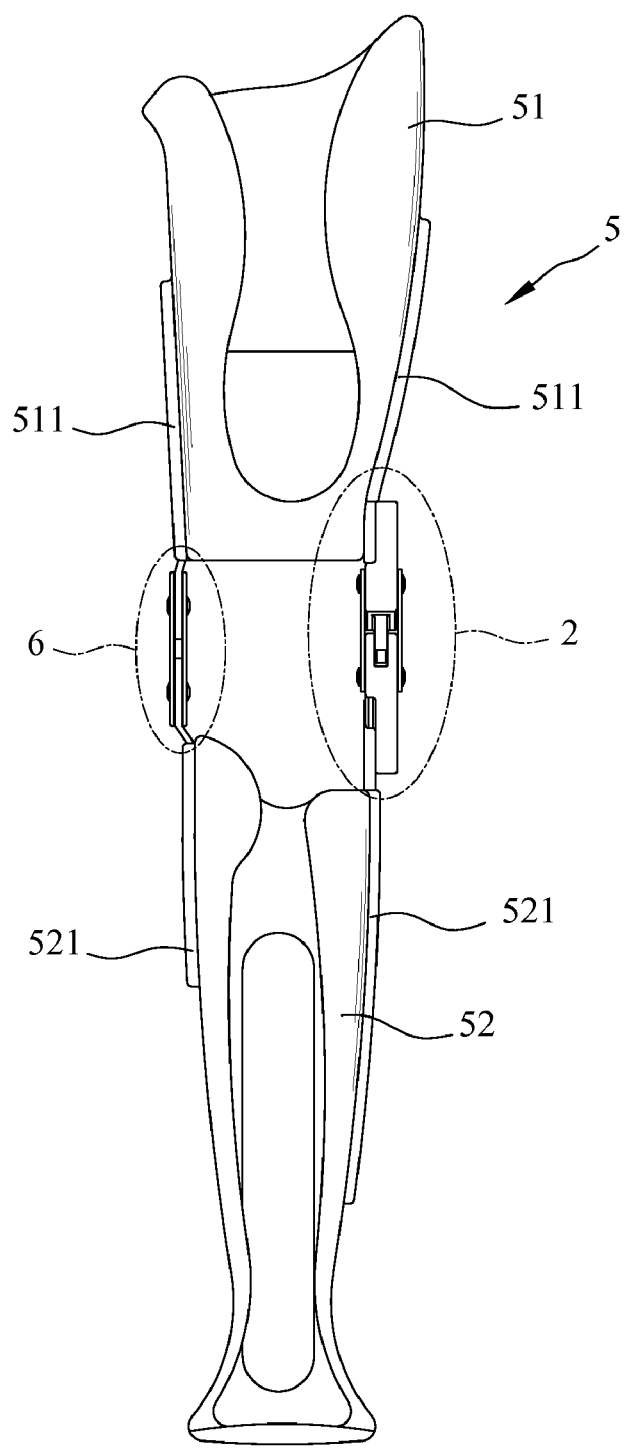
FIG. 10 is a front view of FIG. 8.

FIGS. 9 and 10 are schematic views showing that the artificial knee joint of the present invention is assembled in a joint of a leg brace 5. The leg brace 5 includes an upper support rod 511 and a lower support rod 521 respectively connected with two sides of an upper socket 51 and a lower socket 52. Moreover, the aforementioned four-bar linkage 2 is connected between the upper support rod 511 and the lower support rod 521 at one side of the upper socket 51 and the lower socket 52. A regular pivotal joint 6 is connected between the upper support rod 511 and the lower support rod 521 at the other side of the upper socket 51 and the lower socket 52. With the artificial knee joint of the present invention, the beg brace 5 does not produce unexpected wobbles in the swing phase, and can provide enough support in the stance phase. In addition, the leg brace can be operated or moved in agility, thereby saving the user's energy and reducing occurrence of accidental falls.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An artificial knee joint, comprising:
a four-bar linkage;
an extension bar having a first end pivotally connected to the four-bar linkage; and
a restoring device, connected to a bottom of the four-bar linkage and comprising a transmission rod having a first end pivotally connected to and retractably moving a second end of the extension bar, wherein
the four-bar linkage comprises a first connecting bar, a second connecting bar, a third connecting bar, and a fourth connecting bar, wherein a first end of a first connecting bar and a second end of a second connecting bar are pivotally connected together by a first pivot axle, a first end of a second connecting bar and a second end of a third connecting bar are pivotally connected together by a second pivot axle, a first end of a third connecting bar and a second end of a fourth connecting bar are pivotally connected together by a third pivot axle, a first end of a fourth connecting bar and a second end of a first connecting bar are pivotally connected together by a fourth pivot axle,
a first straight line joins the first pivot axle and the second pivot axle, a second straight line joins the second pivot axle and the third pivot axle, a third straight line joins the third pivot axle and the fourth pivot axle, and a fourth straight line joins the fourth pivot axle and the first pivot axle,
the first end of the extension bar is pivotally connected to the fourth pivot axle, by means of the actions of gravity and the restoring device on the extension bar and further on the fourth pivot axle, the four-bar linkage is expanded to a limited state or a locked state, at this moment an included angle $\theta_1$ defined between the first straight line and the second straight line is between 21°-23°, an included angle $\theta_2$ defined between the second straight line and the third straight line is between 159°-161°, an included angle $\theta_3$ defined between the third straight line and the fourth straight line is between 97°-99°, and an included angle $\theta_4$ defined between the fourth straight line and the first straight line is between 78°-80°.

2. The artificial knee joint according to claim 1, wherein the restoring device further comprises a body and an extension-biasing spring, the extension-biasing spring and the transmission rod are assembled in the body, a first end of the extension-biasing spring is biased against a second end of the transmission rod and a second end of the extension-biasing spring is biased against a bottom of the body.

3. The artificial knee joint according to claim 1, wherein the restoring device is a pneumatic cylinder.

4. The artificial knee joint according to claim 1, wherein the restoring device is a hydraulic cylinder.

* * * * *